United States Patent [19]
Allard et al.

[11] Patent Number: 5,309,648
[45] Date of Patent: May 10, 1994

[54] ORTHOPAEDIC GAUGE

[75] Inventors: Randall N. Allard, Plymouth; Bradley T. Durcholz, Warsaw, both of Ind.

[73] Assignee: Zimmer, Inc., Warsaw, Ind.

[21] Appl. No.: 48,340

[22] Filed: Apr. 15, 1993

[51] Int. Cl.⁵ .............................................. G01B 5/02
[52] U.S. Cl. ...................................... 33/783; 33/567; 33/511
[58] Field of Search ....................... 33/783, 549, 555.2, 33/562, 563, 565, 567, 199 R, 199 B, 511, 501.45

[56] References Cited

U.S. PATENT DOCUMENTS

| | | | |
|---|---|---|---|
| 926,688 | 6/1909 | Carroll | 33/562 |
| 2,677,892 | 5/1954 | Schecter | |
| 3,230,628 | 1/1966 | Hite | 33/199 R |
| 3,318,006 | 5/1967 | Martinez | 33/562 |
| 4,584,774 | 4/1986 | Link | 33/567 X |

OTHER PUBLICATIONS

Zimmer Catalog-1987-pp. B97, B100, B102.
Zimmer Catalog-1978-p. B134.

*Primary Examiner*—William A. Cuchlinski, Jr.
*Assistant Examiner*—Alvin Wirthlin
*Attorney, Agent, or Firm*—Margaret L. Geringer

[57] ABSTRACT

An orthopaedic gauge 1 for measuring a length dimension of an elongated orthopaedic device, such as a screw 50, 60, or 70 or a pin or other elongated orthopaedic device. The gauge 1 includes a base portion 10 having a fixed reference point thereon, such as a raised post 12, and a raised platform 20 extending from the base portion 10 and spaced from the reference point. The raised platform 20 includes a plurality of stops 22. One end of the orthopaedic device is positioned about the reference point and the device is swung through an arc about the reference point until the other end of the device abuts one of the plurality of stops on the raised platform. A suitable scale such as 38 or 39 is provided to correspond with the plurality of stops for determining a length dimension of the device.

12 Claims, 2 Drawing Sheets

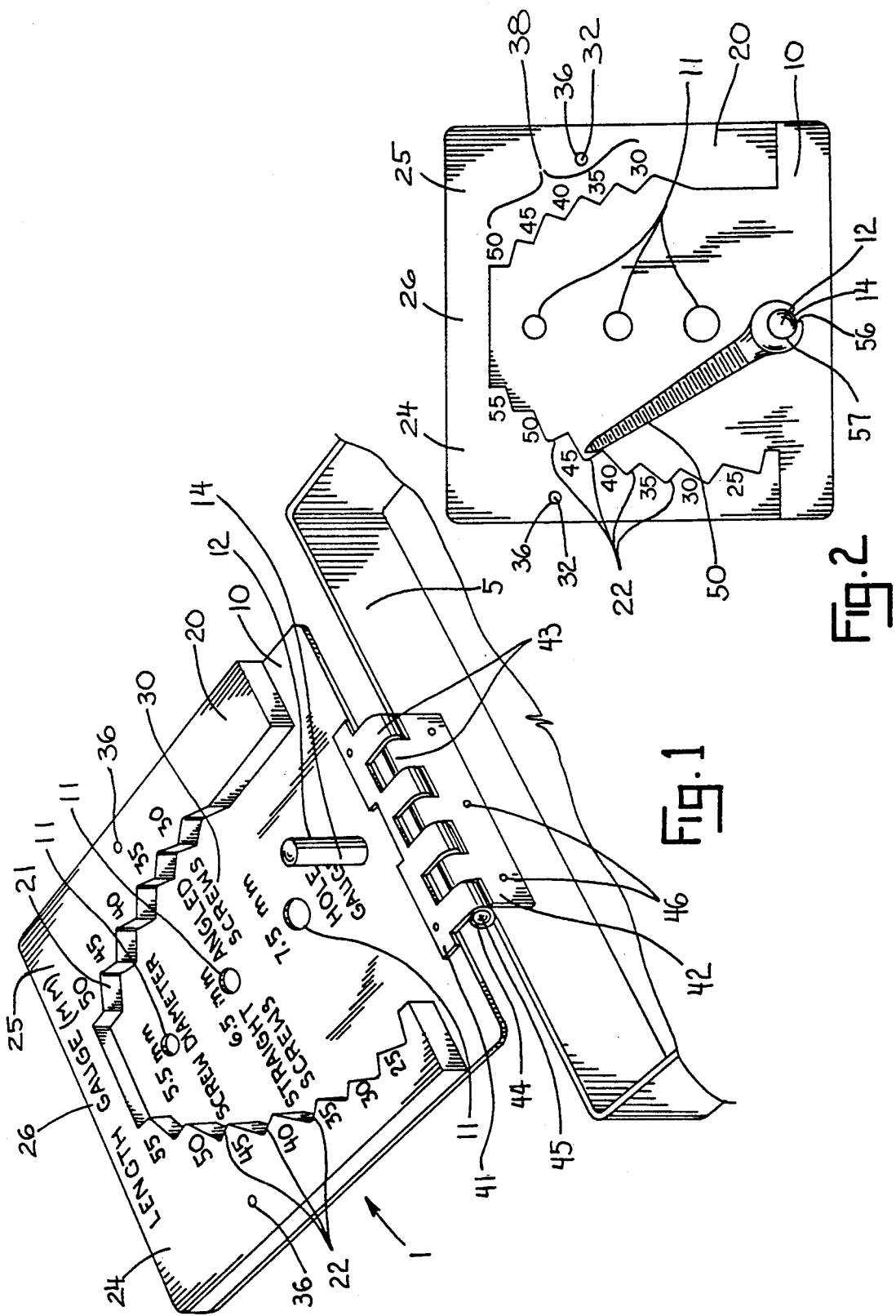

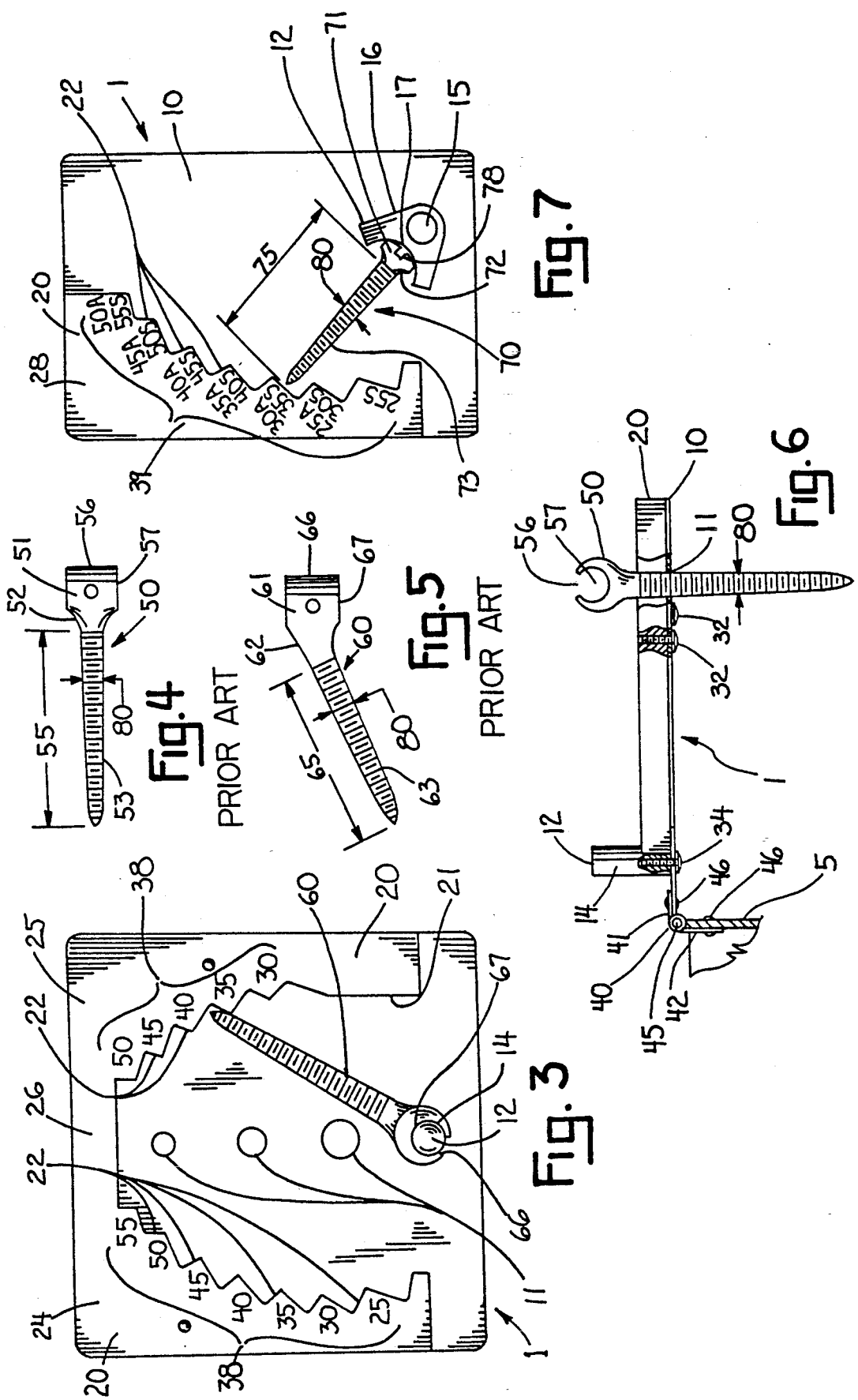

ORTHOPAEDIC GAUGE

FIELD OF THE INVENTION

The invention relates to the field of orthopaedic gauges. In particular, this invention relates to such gauges for measuring a length dimension of an elongated orthopaedic device, such as a screw or pin or other such device.

BACKGROUND OF THE INVENTION

In the field of orthopaedics, it is often necessary to use a length gauge to either measure the overall length of a device or to measure the length of a portion of the device, such as the length of screw threads. Typically, bone screws or pins or the like are measured by a longitudinal or straight scale such that the elongated device to be measured is positioned against or alongside such a straight scale and compared thereto to determine a length dimension.

An example of such a straight gauge for measuring orthopaedic screws is disclosed in U.S. Pat. No. 3,230,628 to James Hite.

SUMMARY OF THE INVENTION

The present invention provides an orthopaedic gauge for measuring a length dimension of an elongated orthopaedic device such as a screw or a pin or other elongated orthopaedic device. The gauge includes a based portion having a fixed reference point thereon, such as a raised post, and a raised platform extending from the base portion and spaced from the reference point. The raised platform includes a plurality of stops. One end of the orthopaedic device is positioned about the reference point and the device is swung through an arc about the reference point until the other end of the device abuts one of the plurality of stops on the raised platform. A suitable scale is provided to correspond with the plurality of stops for determining a length dimension of the device.

Accordingly, it is an advantage of the invention to provide a novel orthopaedic gauge which provides a positive stop for determining a length dimension of an elongated orthopaedic device.

Another advantage of the invention is to provide a simple and accurate gauge for determining the proper length device.

A further advantage of the invention is to provide such a gauge which provides for a dual scale which can be used to correspond to two different types of measurement parameters, such as for two different types of devices with different length features.

Still other advantages of the invention will become apparent upon reference to the accompanying drawings.

BRIEF DESCRIPTION OF THE DRAWINGS

FIG. 1 is a perspective view of an orthopaedic gauge in accordance with the present invention.

FIG. 2 is a top plan view of the gauge of FIG. 1 shown in conjunction with a straight screw.

FIG. 3 is a top plan view of the gauge of FIG. 1 shown in conjunction with an angled screw.

FIG. 4 is a side elevational view of the straight screw of FIG. 2.

FIG. 5 is a side elevational view of the angled screw of FIG. 3.

FIG. 6 is a side elevational view of the gauge of FIG. 1 shown in conjunction with a straight screw.

FIG. 7 is a top plan view of an alternate embodiment for the gauge of the present invention shown in conjunction with an alternate style of screw.

DESCRIPTION OF THE PREFERRED EMBODIMENT

The preferred embodiment described herein is not intended to be exhaustive or to limit the invention to the precise form disclosed. Rather it is chosen and described to best explain the invention so that others skilled in the art might utilize its teachings.

Accordingly, FIGS. 1-6 illustrate the preferred embodiment of an orthopaedic gauge in accordance with the present invention. This invention relates to gauges for measuring a length dimension of an elongated orthopaedic device, such as a screw or pin or other such elongated device. The invention will be described with reference to screw devices, such as spinal screws or other fracture fixation bone screws. However, it is understood that the invention is not limited thereto, and that the features of the invention could be adapted for measuring a length dimension of other elongated devices.

The gauge 1 may be utilized separately or it may be attached to a suitable product case 5 such as by hinge 40 as shown in FIGS. 1 and 6. Hinge 40 may include a gauge side hinge portion 41 and a case side hinge portion 42, each side including interconnecting hinge fingers 43. The hinge fingers 43 form a hinge channel 44 through which interconnecting hinge rod 45 can be inserted to hingedly attach the gauge 1 to case 5. The hinge portions 41 and 42 may be secured to the gauge 1 and case 5, respectively, by rivets 46 or other suitable securing mechanism.

The gauge 1 includes a base portion 10 having a fixed reference point thereon, such as raised post 12, and a raised platform 20 extending from base portion 10. Raised platform 20 is spaced from post 12 and includes a plurality of stops 22. One end of the elongated orthopaedic device is positioned about the fixed reference point or post 12, while the other end of the device, such as screw 50 or 60 (in FIGS. 2 and 3) abuts one of the plurality of stops 22 on raised platform 20 to provide a positive indication of a length dimension of the screw 50 or 60. The screw 50 or 60 can be swung through an arc about the reference point or post 12 until the other end abuts one of the plurality of stops 22 on raised platform 20. The plurality of stops 22 are arranged in an arc about the reference point of post 12. The raised post 12 shown in FIGS. 1-3, and 6 is a cylindrical post having a cylindrical surface 14 for accepting a corresponding cylindrical channel 57 or 67 in screws 50 or 60, respectively.

While it is particularly advantageous for the fixed reference point to be a raised portion such as raised post 12 to cooperate with an end of the elongated orthopaedic device, it is also possible for the fixed reference to be some other type of fixed reference point, such as a hole or recess (not shown) in base portion 10 for cooperating with a suitable mating portion on the elongated orthopaedic device.

The gauge 1 includes a scale, such as 38 thereon to identify a length dimension to correspond to each stop 22 of the plurality of stops. The scale 38 may be designed or set up to measure a desired length dimension for particular components. For example, the scale may be set up to measure the overall length dimension of an orthopaedic device, or in the case of the screws 50 or 60 shown in FIGS. 4 and 5, respectively, the scale 38 may be set up to measure the length 55 or 65 of the screw threads 53 or 63 on screws 50 or 60, respectively. In this case, the scale takes into account the length of the nonthreaded portion of screws 50 or 60 in order to provide such a scale 38. Thus, the length of the nonthreaded portion of screws 50 or 60 is kept constant for a particular scale used for a corresponding set of varying length screws.

Thus, the gauge 1 may also provide a scale 38 which is a dual scale which can be used to correspond to two different types of measurement parameters. For the gauge of FIGS. 1-3 and 6, the raised platform 20 of gauge 1 provides a first side 24 and a second side 25 interconnected by connecting portion 26. Accordingly, the dual scale 38 provides a first set of numbers on first side 24 to identify thread length for a first type of device, such as straight screws 50 and a second set of numbers to identify thread length of a second type of device, different from the first type, such as angled screws 60.

The reason the straight screws 50 and angled screws 60 shown in FIGS. 4 and 5, respectively, require a different scale to measure thread length is that the nonthreaded portion of each of these two different style of screws is different. The nonthreaded portion of straight screw 50 (see FIG. 4) includes head 51 and neck 52 which interconnects the head 51 with threads 53. This nonthreaded length dimension is kept constant for the series of straight screws 50 to be measured, so that the series of screws can include varying lengths of threads which can then be measured by gauge 1. The scale 38 is set up to take into account the nonthreaded length, so that the number read at the stop 22 where the screw abuts is the length of the threaded portion of the screw.

With the angled screws (FIG. 5) the nonthreaded portion includes head 61 and neck 62 to interconnect head 61 and threads 63. The neck 62 is relatively longer than the neck 52 of the series of straight screws 50 to account for the angled transition of the screw 60. Accordingly, the length of the nonthreaded portion of the series of varying length angled screws 60 is kept constant for this series of angled screws 60, and is slightly longer than the length of the nonthreaded portion of the series of varying lengths of straight screws 50. In the scale 38 shown in FIGS. 1-3, the scale for the straight screws 50 is on the first side 24, and the scale for the angled screws 60 is on the second side 25 of gauge 1. Graphics 30 may be provided on the gauge 1 to indicate which side of the gauge is for straight screws and which side is for angled screws, as shown in FIG. 1. These graphics may be silk screened onto the gauge 1 or provided in any other suitable manner.

For the gauge 1 of FIGS. 1-3, it is noted that the unthreaded portion of the angled screws 60 is 5 mm longer than the unthreaded portion of straight screws 50. Thus, the scale 38 accounts for this difference between the two sides of the dual scale, such that a particular arc or radial distance from the fixed reference point on first side 24 of gauge 1 reflects a 5 mm longer length of screw threads for a comparable radial distance from the fixed reference point on second side 25 of gauge 1. (See FIGS. 2 and 3, for reference.)

The screws 50 and 60 of FIGS. 4 and 5, respectively, each include a cylindrical channel 57 or 67 for fitting about the cylindrical surface 14 of post 12. These screws 50 and 60 may include an open back 56 and 66, respectively, which leads into channel 57 or 67. The cylindrical channels 57 and 67 at one end of screws 50 and 60, respectively, are particularly advantageous for enabling screws 50 or 60 to swing in an arc about fixed reference point or the cylindrical surface 14 of post 12, although other suitable interacting mechanisms can be utilized.

The plurality of stops 22 are formed on an inner wall portion 21 of raised platform 20 facing toward post 12. The inner wall portion 21 may be comprised of a series of interconnecting steps to form stops 22, such that the interconnecting steps are arranged in a series of arcs about the fixed reference point or raised post 12. Both the first side 24 and second side 25 of gauge 1 include a plurality of stops 22 thereon. These steps or stops 22 may be substantially L-shaped, so that as an orthopaedic device such as screw 50 or 60 is swung in an arc about post 12, positioned with one end of the device aligned at post 12, the other end of the device will abut a leg of one of the corresponding L-shaped stops 22, using the corresponding side of the gauge for straight or angled screws, accordingly. The stops 22 provide a positive indication of the length of threads on screws 50 or 60, and can be read from scale 38.

Thus, to determine the thread length 55 or 65, place channel 57 or 67 of the screw 50 or 60, respectively, over post 12. The screw may be swung about the cylindrical surface 14 of post 12 counterclockwise for straight screws 50 and clockwise for angled screws 60. The head 61 of angled screws 60 should be put on the post 12 such that the shaft of the screw 60 appears to point downward toward the base portion 10. The scale for the angled screws 60 is preferably set up to take this positioning into account. The scale 38 on the first side 24 (or left side) is set up for the straight screws 50 and the scale 38 on the second side 25 (or right side) is set up for the angled screws 60. Different colors may be used to distinguish one side of scale 38 from the other. Angled screws, as known in the art, typically provide a screw 60 in which the axis of the threaded portion 53 of screw 60 is angled with respect to the head 61.

The gauge 1 also may include a plurality of different size through holes 11 for measuring the diameter 80 of the elongated orthopaedic device. To determine the diameter of the orthopaedic device, such as a screw, place the device through the smallest gauge hole that will allow the shaft of the screw to pass through the hole 11. FIG. 6 shows a straight screw 50 being inserted into a hole 11.

The post 12 may be secured the base portion 10 via connecting screw 34 which is threaded into a corresponding hole in the base portion 10 and in post 12 as shown in FIG. 6. The raised portion 20 may be secured the base portion 10 via connecting screws 32 which are threaded into corresponding holes 36 through the base portion 10 and raised portion 20. Two screws 32 may be provided to secure raised portion 20, one on first side 24 and one on second side 25. One screw 32 may be oriented lower than the other relative to the top of gauge 1 so that the raised portion 20 cannot be put on upside down during assembly. This is important since the sides 24 and 25 are not symmetrical. The graphics 30, if silk screened, would typically be added on after the raised platform 20 has been attached to base portion 10.

Any suitable manufacturing methods and materials may be utilized. For example, the base portion 10 and raised platform 20 of gauge 1 may conveniently be made of aluminum with connecting screws 32 and 34 and post 12 made of stainless steel. Alternatively, the gauge could be molded in a single piece from a plastic material, if desired. The graphics 30 and scale 38 could even be directly molded into or onto the plastic.

FIG. 7 shows an alternate embodiment for the gauge 1 of the present invention. The gauge 1 of FIG. 7 includes a single series of steps 22 arranged in an arc about post 12. This gauge 1 includes base portion 10 with raised platform 20 with the single series of steps 22 provided on a single side 28. A dual scale may also be provided with the embodiment of FIG. 7, utilizing two different type of scale parameters on the single side 28 using the same series of steps 22 as shown at scale 39 in FIG. 7. A first set of numbers is provided to identify the thread length 55 for straight screws 50 as designated by the "S" after the first set of numbers, and a second set of numbers is provided to identify the thread length 65 for angled screws 60 as designated by the "A" after the second set of numbers. Alternatively, the numbers could be shown in different colors to differentiate the two different series of thread length designations.

It is pointed out that more than two different scales could be provided, if desirable, or different scales could be set up relative to different fixed reference points on a single gauge, if desirable.

FIG. 7 also shows an alternate design for raised post 12 in which post 12 is comprised of a raised block 16 having a positioning portion such as recess 17 for accepting one end of an elongated orthopaedic device, such as screw 70. The block may be pivotally attached to base portion 10, if desired. For example, block 16 may be pivotally fitted about a central cylindrical rod 15 or otherwise pivotally attached. The positioning portion 17 may be any suitable shape for accepting one end of the orthopaedic device. The head 71 of screw 70 does not include a channel as did screws 50 and 60. However, screw 70 may include a screw driving recess 78 on head 71 which is connected to threads 73 via neck 72. The scale 39 may be set up to measure thread length 75 of screw 70 or some other predetermined length dimension of screw 70, as desired.

While this invention has been described in terms of a particularly advantageous embodiment, those skilled in the art can appreciate that modifications can be made without departing from the spirit and scope of this invention.

We claim:

1. An orthopaedic gauge including a means for measuring a length dimension of an elongated orthopaedic device, wherein the means for measuring includes a base portion having a fixed reference point thereon and a raised platform extending from the base portion and spaced from the reference point, wherein the raised platform includes a plurality of stops, and wherein the means for measuring further includes a means for positioning one end of the elongated orthopaedic device about the fixed reference point to enable the device to be swung through an arc about the reference point until the other of the device abuts one of the plurality of stops on the raised platform, and wherein the gauge includes a scale thereon to identify a length dimension to correspond to at least one of the plurality of stops.

2. The orthopaedic gauge of claim 1 wherein the means for positioning comprises a raised post extending from the base portion at the fixed reference point.

3. The orthopaedic gauge of claim 2 wherein the raised post has a cylindrical surface providing a means for accepting a corresponding cylindrical channel in the elongated orthopaedic device to enable the device to be swung through an arc about the cylindrical surface of the post.

4. The orthopaedic gauge of claim 2 wherein the raised post is a block having a positioning portion providing a means for accepting one end of the elongated orthopaedic device.

5. The orthopaedic gauge of claim 4 wherein the block includes a pivotal attachment means for pivotally attaching the block to the base portion.

6. An orthopaedic gauge for measuring a length dimension of an elongated orthopaedic device, wherein the gauge includes a base portion having a fixed reference point thereon and a raised platform extending from the base portion and spaced from the reference point, wherein the raised platform includes a plurality of stops, and wherein one end of the elongated orthopaedic device is positioned about the fixed reference point and the device is swung through an arc about the reference point until the other end of the device abuts one of the plurality of stops on the raised platform, and wherein the fixed reference point is a single fixed reference point and wherein the raised platform has a first side spaced in one direction from the single reference point and a second side spaced in a second direction from the single reference point, different from the first direction and wherein the plurality of stops includes a first plurality of stops on the first side of the platform and a second plurality of stops on the second side of the platform, and wherein the gauge includes a scale thereon to identify a length dimension to correspond to at least one of the plurality of stops.

7. The orthopaedic gauge of claim 6 wherein the scale includes a first scale on the side to identify the length dimension to correspond to the distance between the reference point and each stop of the first plurality of stops and wherein the scale further includes a second scale on the second side to identify the length dimension to correspond to the distance between the reference point and each stop of the second plurality of stops.

8. A method of measuring a length dimension of an elongated orthopaedic device comprising the following steps:
   a) providing an orthopaedic gauge including a base portion having a fixed reference point thereon and a raised platform extending from the base portion and spaced from the reference point, and wherein the raised platform includes a plurality of stops;
   b) positioning one end of the elongated orthopaedic device at the fixed reference point; and
   c) swinging the device through an arc about the reference point until the other end of the device abuts one of the plurality of stops on the raised platform.

9. The method of claim 8 wherein the fixed reference point comprises a raised post extending from the base portion, the raised post including a cylindrical surface, and wherein the one end of the elongated orthopaedic device includes a corresponding cylindrical channel, so that the positioning step further includes positioning the cylindrical channel of the device about the cylindrical surface of the post, and the swinging step includes swinging the cylindrical channel of the device about the cylindrical surface of the post.

10. The method of claim 8 further including the step of providing a scale on the gauge to identify a length dimension to correspond to the plurality of stops.

11. The method of claim 8 wherein the fixed reference point is a single fixed reference point and wherein the raised platform has a first side spaced in one direction from the single reference point and a second side spaced in a second direction from the single reference point, different from the first direction and wherein the plurality of stops includes a first plurality of stops on the first side of the platform and a second plurality of stops on the second side of the platform, and wherein the method further includes the step of swinging a first type of orthopaedic device through an arc toward the first side of the platform until the first type of device abuts one of the first plurality of stops on the first side or swinging a second type of orthopaedic device, different from the first type, through an arc toward the second side of the platform until the second type of device abuts one of the second plurality of stops on the second side.

12. The method of claim 11 wherein the method further includes providing a first scale on the first side of the platform to identify the length dimension to correspond to the distance between the reference point and each stop of the first plurality of stops and providing a second scale on the second side of the platform to identify the length dimension to correspond to the distance between the reference point and each stop of the second plurality of stops.

* * * * *